US011315246B2

United States Patent
Innanje et al.

(10) Patent No.: US 11,315,246 B2
(45) Date of Patent: Apr. 26, 2022

(54) CARDIAC FEATURE TRACKING (71) Applicant: SHANGHAI UNITED IMAGING INTELLIGENCE CO., LTD., Shanghai (CN)

(72) Inventors: Arun Innanje, Lexington, MA (US); Xiao Chen, Lexington, MA (US); Shanhui Sun, Lexington, MA (US); Terrence Chen, Lexington, MA (US)

(73) Assignee: SHANGHAI UNITED IMAGING INTELLIGENCE CO., LTD., Shanghai (CN)

(*) Notice: Subject to any disclaimer, the term of this patent is extended or adjusted under 35 U.S.C. 154(b) by 51 days.

(21) Appl. No.: 17/014,609

(22) Filed: Sep. 8, 2020

(65) Prior Publication Data
US 2021/0157464 A1 May 27, 2021

Related U.S. Application Data (60) Provisional application No. 62/941,198, filed on Nov. 27, 2019.

(51) Int. Cl.
G06T 7/12 (2017.01)
G06T 7/00 (2017.01)
G06T 7/11 (2017.01)
G06K 9/62 (2022.01)
G06N 3/04 (2006.01)
(Continued)

(52) U.S. Cl.
CPC .......... *G06T 7/0012* (2013.01); *A61B 5/0044* (2013.01); *A61B 5/1128* (2013.01); *A61B 5/7264* (2013.01); *G06F 3/0485* (2013.01); *G06K 9/6267* (2013.01); *G06N 3/0454* (2013.01); *G06N 3/08* (2013.01); *G06T 3/0093* (2013.01); *G06T 7/0014* (2013.01); *G06T 7/11* (2017.01); *G06T 7/248* (2017.01); *G06T 7/55* (2017.01); *G06T 7/73* (2017.01); *G06T 11/206* (2013.01); *G06T 13/80* (2013.01); *G06T 19/00* (2013.01); *G16H 30/40* (2018.01); *G16H 50/30* (2018.01); *G16H 50/50* (2018.01); *G06T 2200/24* (2013.01); *G06T 2207/10016* (2013.01); *G06T 2207/20081* (2013.01);
(Continued)

(58) Field of Classification Search
CPC ..................................... G06T 7/0012
USPC .......................................... 715/771
See application file for complete search history.

(56) References Cited

U.S. PATENT DOCUMENTS

RE43,637 E * 9/2012 Miyazaki ........... G01R 33/5635
324/314
9,176,211 B2 * 11/2015 Cupps ............... G01R 33/56333
(Continued)

*Primary Examiner* — Reza Nabi
(74) *Attorney, Agent, or Firm* — Zhong Law, LLC (57) ABSTRACT Cardiac features captured via an MRI scan may be tracked and analyzed using a system described herein. The system may receive a plurality of MR slices derived via the MRI scan and present the MR slices in a manner that allows a user to navigate through the MR slices. Responsive to the user selecting one of the MR slices, contextual and global cardiac information associated with the selected slice may be determined and displayed. The contextual information may correspond to the selected slice and the global information may encompass information gathered across the plurality of MR slices. A user may have the ability to navigate between the different display areas and evaluate the health of the heart with both local and global perspectives.

17 Claims, 7 Drawing Sheets (51) Int. Cl.

| | |
|---|---|
| *G16H 50/50* | (2018.01) |
| *G16H 50/30* | (2018.01) |
| *G16H 30/40* | (2018.01) |
| *G06F 3/0485* | (2022.01) |
| *G06T 11/20* | (2006.01) |
| *G06T 13/80* | (2011.01) |
| *G06T 19/00* | (2011.01) |
| *G06T 7/55* | (2017.01) |
| *G06T 7/73* | (2017.01) |
| *G06T 7/246* | (2017.01) |
| *A61B 5/00* | (2006.01) |
| *A61B 5/11* | (2006.01) |
| *G06T 3/00* | (2006.01) |
| *G06N 3/08* | (2006.01) |

(52) U.S. Cl.
CPC ............ *G06T 2207/20084* (2013.01); *G06T 2207/30048* (2013.01); *G06T 2210/41* (2013.01)

(56) References Cited

U.S. PATENT DOCUMENTS

| | | | | |
|---|---|---|---|---|
| 9,629,615 | B1* | 4/2017 | Tavakoli | G06T 7/269 |
| 2003/0071810 | A1* | 4/2003 | Shoov | G06F 30/00 |
| | | | | 345/420 |
| 2004/0143189 | A1* | 7/2004 | Lysyansky | A61B 8/485 |
| | | | | 600/450 |
| 2009/0002366 | A1* | 1/2009 | Kanitsar | A61B 6/466 |
| | | | | 345/419 |
| 2009/0123412 | A1* | 5/2009 | Healy | A61L 27/16 |
| | | | | 424/78.17 |
| 2010/0022901 | A1* | 1/2010 | Breeuwer | A61B 5/1075 |
| | | | | 600/508 |
| 2010/0057618 | A1* | 3/2010 | Spicer | G06Q 40/06 |
| | | | | 705/64 |
| 2010/0195887 | A1* | 8/2010 | Abe | G06T 7/246 |
| | | | | 382/131 |
| 2013/0002646 | A1* | 1/2013 | Lin | G06T 7/11 |
| | | | | 345/419 |
| 2014/0342984 | A1* | 11/2014 | Matheny | A61L 27/54 |
| | | | | 514/8.9 |
| 2016/0098833 | A1* | 4/2016 | Tsadok | G06K 9/6201 |
| | | | | 382/103 |
| 2016/0196643 | A1* | 7/2016 | Bendall | G06F 3/005 |
| | | | | 382/108 |
| 2017/0065242 | A1* | 3/2017 | Chirvasa | A61B 5/00 |
| 2017/0120080 | A1* | 5/2017 | Phillips | A61B 5/02125 |
| 2017/0337705 | A1* | 11/2017 | Bendall | G06T 7/0004 |
| 2018/0042497 | A1* | 2/2018 | Cowan | G01R 33/56308 |
| 2018/0232878 | A1* | 8/2018 | Braun | G06T 7/20 |
| 2019/0053760 | A1* | 2/2019 | Gerald, II | A61B 5/055 |
| 2019/0125309 | A1* | 5/2019 | Ramm | A61B 5/352 |
| 2019/0332189 | A1* | 10/2019 | Mandel-Iaia | G06F 3/023 |
| 2020/0209370 | A1* | 7/2020 | Zhang | G01S 13/931 |
| 2020/0214662 | A1* | 7/2020 | Konofagou | A61B 5/339 |
| 2021/0157464 | A1* | 5/2021 | Innanje | G06T 7/73 |
| 2021/0158543 | A1* | 5/2021 | Sun | G06K 9/6271 |

* cited by examiner

CARDIAC FEATURE TRACKING

CROSS-REFERENCE TO RELATED APPLICATIONS

This application claims the benefit of Provisional U.S. Patent Application No. 62/941,198, filed Nov. 27, 2019, the disclosure of which is incorporated herein by reference in its entirety.

BACKGROUND

Cardiovascular diseases are the leading cause of death globally, taking an estimated 17.9 million lives each year. Accurate assessment of cardiac features and functions is pivotal for preventing and treating these diseases. In recent years, cardiac magnetic resonance imaging (cMRI) has emerged as a powerful tool for evaluating cardiac features including strains, strain-rates, torsions and/or mechanical dispersions. It allows for precise quantification of ventricular and atrial mechanics by directly evaluating myocardial fiber deformation, without subjecting patients to radiation or invasive procedures.

While cMRI can provide abundant information about the health of the heart, there is currently a lack of tools for interfacing with a cMRI device, understanding the information captured by the cMRI device, or organizing and presenting the information captured by the cMRI device in manners that would allow clinicians to fully utilize the advantages of cMRI. For instance, upon acquiring cardiac cine images of the myocardium, it is highly desirable for a clinician to be able to navigate through the images in order to evaluate specific areas of the myocardium based on contextual information associated with those areas. And while focusing on one specific area, it is also desirable to maintain a global perspective of the myocardium, for example, across both time and space, so that changes that have occurred to the one specific area can be viewed in relation to other areas of the myocardium or other points in time.

SUMMARY

Described herein are systems, methods and instrumentalities for tracking and analyzing cardiac features captured via an MRI scan. An MRI analyzer as described herein may receive a plurality of MR slices that may be derived via an MRI scan of a patient's heart (e.g., a cardiac MR cine). The MR slices may correspond to respective scan locations along a scan axis and each of the MR slices may include a visual representation of a myocardium over a time period (e.g., one or more cardiac cycles). The MRI analyzer may present the MR slices, for example, in a first area of a display device. The presentation may be provided in a way that allows a user of the MRI analyzer to navigate through the MR slices along the scan axis. The MRI analyzer may determine and display contextual information associated with a selected slice of the plurality of MR slices, for example, in a second area of the display device. The contextual information may include images of the myocardium associated with the selected MR slice and strains of the myocardium indicated by the images. The display of the contextual information may include an animated presentation of the images associated with the selected MR slice and graphs (e.g., radial and/or circumferential strain curves) that indicate one or more cardiac parameters determined based on the selected MR slice. Responsive to the user selecting a point on the graphs (e.g., along a time axis), the MRI analyzer may adjust the animated presentation of the images of the myocardium to display an image of the myocardium that corresponds to a temporal location of the selected point on the graphs. Further, the animated presentation of the images may indicate an inner boundary and an outer boundary of the myocardium, and the MRI analyzer may be configured to receive user inputs that mark the inner and outer boundaries of the myocardium.

The MRI analyzer described herein may also be configured to determine and display global information associated with the myocardium across the plurality of MR slices, for example, in a third area of the display device. The global information may include strain and/or deformation parameters of the myocardium determined by the MRI analyzer based on the plurality of MR slices. The display of the global information may include a 3D view (e.g., a 3D mesh or pointcloud) of the myocardium segmented based on the plurality of MR slices. The display may also include one or more plots (e.g., bullseye plots) that show the global strain or deformation parameters determined by the MRI analyzer for different segments of the myocardium (e.g., based on maximum, minimum or average strains of each segment of the myocardium during the period of time associated with the MR slices). Responsive to a user selecting an area of the plot that corresponds to a segment of the myocardium, the MRI analyzer may highlight the segment of the myocardium in the 3D view. Further, responsive to the user selecting an area of the 3D view that corresponds one of the plurality of MR slices, the MRI analyzer may determine and display contextual information of the one of the plurality of MR slices in the second area of the display device.

The MRI analyzer described herein may also be configured to determine and display a matrix for indicating various states of the myocardium across space and time. The matrix may comprise a plurality of cells, each of which may correspond to a row that represents a respective MR slice among the plurality of MR slices and a column that represents a point in time during the time period associated with the respective MR slice. Hence, each cell of the matrix may indicate a respective state of the myocardium as indicated by the respective MR slice and the point in time associated with the cell.

The MRI analyzer described herein may also be configured to generate, transmit and/or print a report that includes at least a portion of the contextual information or the global information described herein. The report may be generated automatically or semi-automatically, for example, based on a user input that may include textual or oral instructions regarding the report.

BRIEF DESCRIPTION OF THE DRAWINGS

A more detailed understanding of the examples disclosed herein may be had from the following description, given by way of example in conjunction with the accompanying drawing.

DETAILED DESCRIPTION

The present disclosure is illustrated by way of example, and not by way of limitation, in the figures of the accompanying drawings. For example, embodiments will be described herein using cardiac MRI (cMRI) and/or the human heart (e.g., the left ventricle and/or myocardium) as examples, but a skilled person in the art will appreciate that the techniques disclosed herein are generally applicable to other imaging modalities and other organs or tissues of the human body.

Figure 1:
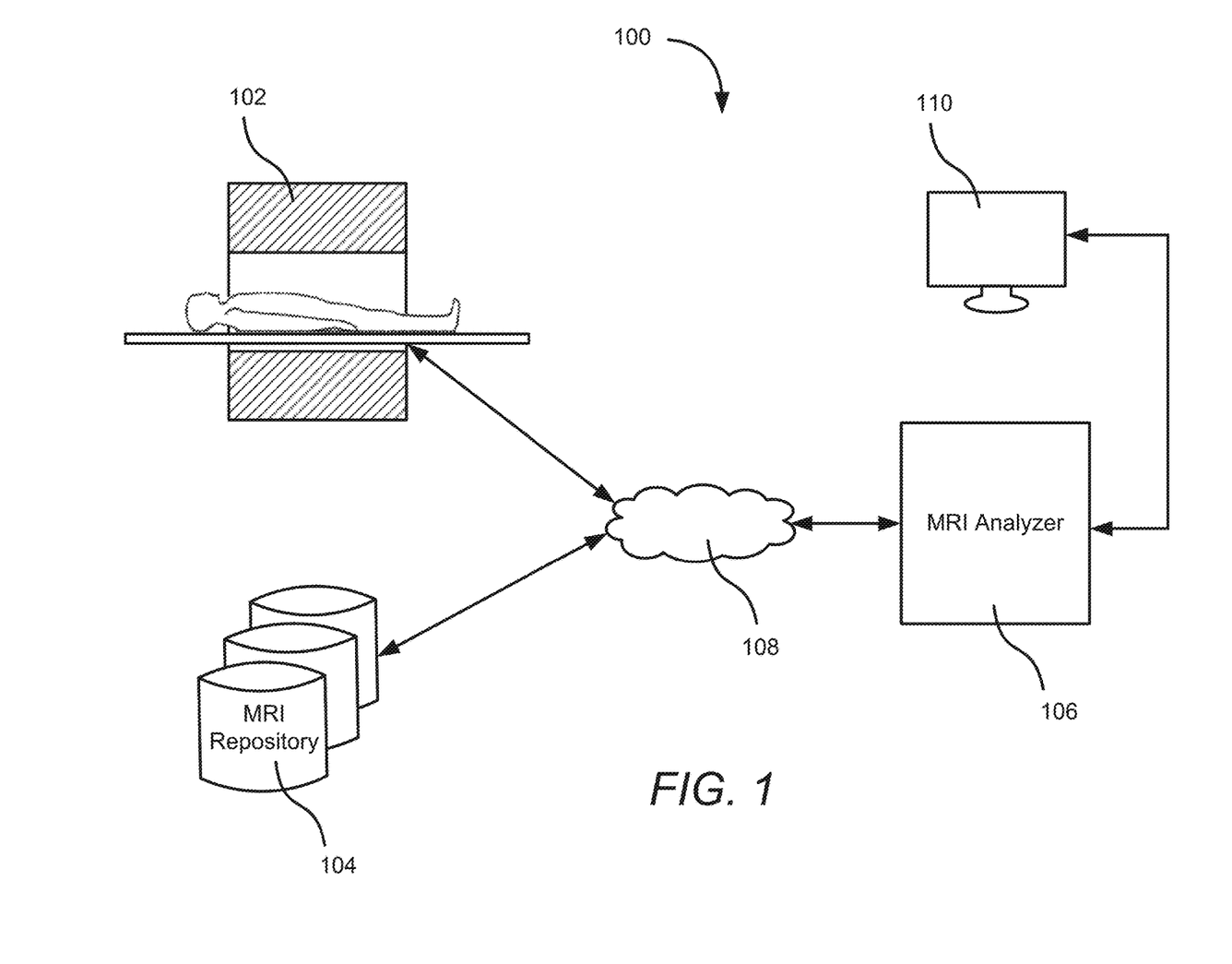
FIG. 1 is a block diagram illustrating an example system that includes an MRI analyzer as described herein.

FIG. 1 is a block diagram illustrating an example magnetic resonance imaging (MRI) feature tracking system 100 according to one or more of the embodiments disclosed herein. The system 100 may include an MRI acquisition device 102, an MRI image repository 104, and/or an MRI analyzer system or device 106. The MRI acquisition device 102 may include a scanner and a controller. The scanner may be implemented using certain types of superconducting magnets having specific bore diameters and/or field strengths. The magnets may generate magnetic fields that are used by the scanner to acquire MR images of a patient positioned within a measurement space. The controller may be configured to control the operation of the MRI acquisition device 102 and may include one or more of an activation unit, a receiver unit, or a data processing module. The activation unit may be used to start and stop the generation of the magnetic fields by the scanner. The receiver unit may be configured to receive and/or record MR data acquired by the scanner, which may then be prepared by the data processing unit for storage and/or further processing.

The data produced by the MRI acquisition device 102 may include one or more dynamic image sequences such as a cardiac cine movie that shows heart motion throughout one or more cardiac cycles. The cardiac cine may include sequences of images taken at respective slice locations along a scan axis (e.g., a short- or long-axis) and over a time frame (e.g., over one or more cardiac cycles). Each such sequence of images may be referred to herein as a slice or an MR slice and each slice may visually represent all or a part of the heart (e.g., the left ventricle, the myocardium, etc.) over the corresponding time frame. For example, a slice may include images of the left ventricle that may be used to determine a systolic output and/or an end diastolic volume, from which a left ventricular ejection fraction (LVEF) may be calculated (e.g., as the ratio between the systolic output and end diastolic volume) to evaluate cardiac function. As another example, images included in a slice may be used to determine myocardial deformation in various directions, from which radial and/or circumferential strains may be calculated. The radial strain may indicate radially directed myocardial deformation towards the center of the LV cavity and the circumferential strain may indicate LV myocardial fiber shortening along the circular perimeter observed on a short-axis.

The data (e.g., the cardiac cine) produced by the MRI acquisition device 102 may be transmitted to and/or stored in the MRI image repository 104, which may be a part of the MRI acquisition device 102 or a part of a separate computing device such as a cloud-based computing device. The MRI image repository 104 may include one or more general-purpose databases or databases specifically configured to store the images produced by the MRI acquisition device 102. The images may be stored in a structured manner (e.g., in certain formats and/or patterns) and/or may be linked to other information of the patient such as the identity or medical history of the patient. The transport and organization of the data produced by the MRI acquisition device 102 may be performed offline, for example, when the MRI acquisition device 102 and/or the MRI image repository 104 are not in use, or online, for example, when the MRI acquisition device 102 is actively collecting scan images and/or when the MRI image repository 104 is being accessed by other devices or applications.

The data (e.g., the cardiac cine) produced by the MRI acquisition device 102 may also be transmitted to and/or retrieved by the MRI analyzer 106. In some examples, the MRI analyzer 106 may retrieve the data directly from the MRI acquisition device 102 while in other examples the MRI analyzer 106 may retrieve the data from the MRI image repository 104, e.g., after the data have already been transported to the repository. The transmission and/or retrieval of data between the MRI acquisition device 102, the MRI image repository 104, and/or the MRI analyzer 106 may be conducted over a communication network 108, which may be a wired or a wireless network, or a combination thereof. For example, the communication network 108 may be established over a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) or 5G network), a frame relay network, a virtual private network (VPN), a satellite network, and/or a telephone network. The communication network 108 may include one or more network access points. For example, the communication network 108 may include wired and/or wireless network access points such as base stations and/or internet exchange points through which the MRI acquisition device 102, the MRI image repository 104, and/or the MRI analyzer 106 may be connected to exchange data and/or other information. Such exchange may utilize routers, hubs, switches, server computers, and/or any combination thereof.

The MRI analyzer 106 may include one or more processors and/or one or more storage devices configured to store computer-readable instructions that, when executed by the one or more processors, cause the processors to perform one or more of the following functions. For example, the instructions may cause the one or more processors to retrieve MRI data such as a cardiac cine from the MRI acquisition device 102 and/or the MRI image repository 104. Upon acquiring the MRI data, the one or more processors may further identify a plurality of MR slices in the MRI data, which, as described herein, may visually depict the condition and/or motion of the heart (e.g., the left ventricle and/or the myocardium) along a scan axis and over a period of time. The period of time may span across one or more cardiac cycles, each of which may include a diastole phase and a systole phase. The one or more processors of the MRI analyzer 106 may be configured to determine the beginning and/or end of the diastole phase and the systole phase using various techniques including, for example, utilizing a machine-learned (ML) model to automatically predict end of diastole (ED) and end of systole (ES) frames, inferring the beginning and/or end of the diastole phase and the systole phase based on recorded electrocardiogram (ECG) signals, receiving user inputs that mark the ED and/or ES frames, etc.

The one or more processors of the MRI analyzer 106 may be further configured to extract contextual and global information about the condition and/or motion of the heart from the MRI data. The contextual information may be associated with each MR slice in the MRI data and may include quantitative parameters such as strain (e.g., deformation), geometry (e.g., volume), and/or motion parameters of the heart that are determined by the one or more processors based on images included in the MR slice. The global information may be derived based on multiple (e.g., all) MR slices and may include parameters of the heart that are synthesized across the multiple MR slices and/or multiple time periods. As such, the global information may be used by the one or more processors of the MRI analyzer 106 to present a comprehensive view of the heart across both time and space (e.g., three dimensions plus time or 3D+T).

The one or more processors of the MRI analyzer 106 may be configured to present the MR slices, the contextual information and/or the global information described herein on a display device 110. The display device 110 may include one or more monitors such as one or more computer monitors, one or more TV monitors, one or more tablets, and/or one or more mobile devices. The display device 110 may also include one or more speakers, one or more augmented reality (AR) devices (e.g., AR goggles), and/or other accessories configured to facilitate the presentation generated by the MRI analyzer 106. The display device 110 may be part of the MRI analyzer 106 or may be communicatively coupled to the MRI analyzer 106, e.g., via the communication network 108 or another suitable communication link.

Figure 2:
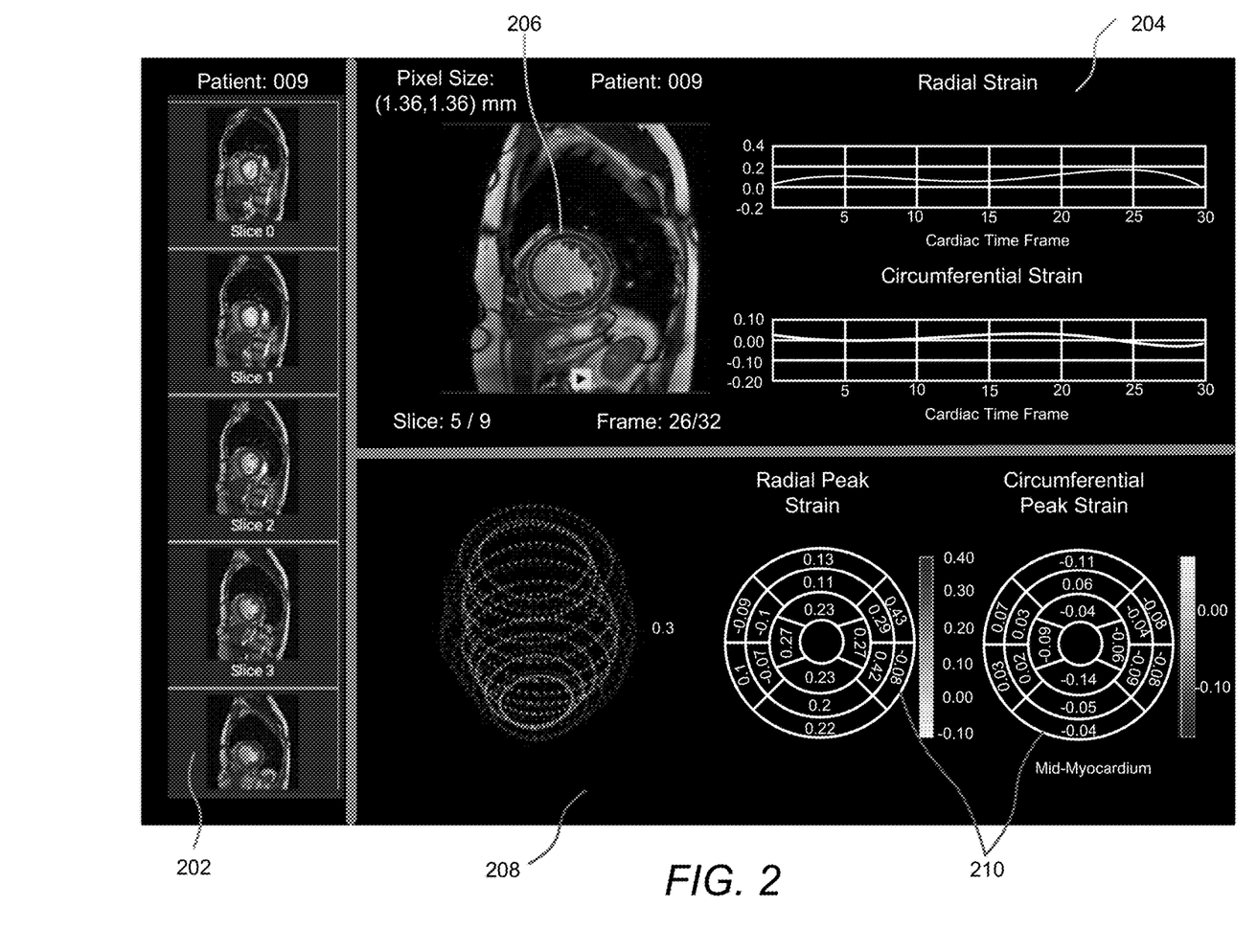
FIG. 2 is a diagram illustrating example information that may be determined and presented by an MRI analyzer as described herein.

FIG. 2 is a diagram illustrating example information that may be determined and presented by the MRI analyzer 106 on a display device such as the display device 110. In a first area 202 of the display device, the MRI analyzer 106 may present patent information (e.g., patent identifier) alongside a navigation pane that allows a user of the MRI analyzer 106 to browse through a plurality of MR slices (e.g., a sequence of MR slices) derived from a cardiac MRI scan of a patient such as a cardiac cine and select a slice that the user is interested in further exploring. The MR slices may be indexed (e.g., labeled), for example, based on their respective locations along a scan axis (e.g., a short- or long-axis). Each MR slice may include multiple MRI images of the heart that collectively provide a visual representation of one or more areas of the heart (e.g., the left ventricle, the myocardium, etc.) over a time period in which the MRI images are taken. As described herein, such a time period may correspond to one or more cardiac cycles and each cardiac cycle may include a diastole phase and a systole phase. The plurality of MR slices displayed in the first area 202 may be switched in and out (e.g., replaced by another set or sequence of MR slices), for example, in response to receiving a user input indicating the switch. For example, the MRI analyzer 106 may obtain difference sequences of MR slices from a same cardiac study of a patient. The MRI analyzer 106 may display icons corresponding to these sequences of MR slices in an area of the display device 110. As a user hovers a mouse over each of the icons or clicks on one of the icons, the MRI analyzer 106 may provide an indication on the display device regarding where the user may drop the sequence of MR slices corresponding to the selected icon. The area into which the user may drop the selected sequence of MR slices may vary depending on the context of the application area that the user is in, and responsive to the user affirmatively dropping the sequence of MR slices into the indicated area, the MRI analyzer 106 may toggle the display in the first 202 to show the sequence of MR slices selected and dropped by the user.

The MRI analyzer 106 may be configured to enable navigation through the plurality of MR slices displayed in the area 202 in various manners. In examples, the MRI analyzer may enable the navigation by providing a sliding bar along a side of the first display area 202 with which a user may scroll through the plurality of MR slices. In examples, the MRI analyzer may include a dropdown menu in a section of the first display area 202 that displays the available MR slices. In examples (e.g., when the display device is touch screen device), the MRI analyzer may utilize a touch surface of the first display area 202 to allow a user to swipe through the MR slices. Selection of a specific slice among the plurality of MR slices may also be performed in various ways. For example, the specific slice may be selected by clicking on an icon that represents the specific slice, by selecting an item on a dropdown menu that corresponds to the specific slice, by tapping in an area of a touch surface in which the specific slice is displayed, by voice activation (e.g., pronouncing the index of the specific slice), etc.

In response to a user selecting a specific MR slice among the plurality of MR slices in the first area 202 of the display device, the MRI analyzer may be configured to determine contextual information associated with the selected MR slice and display the contextual information in a second area 204 of the display device. The contextual information may include one or more series of images (e.g., of the myocardium) that are associated with the selected MR slice and/or quantitative parameters determined based on those images. The images may depict a cross section of the myocardium during the time period (e.g., a cardiac cycle) associated with the selected MR slice. The quantitative parameters may indicate the strain (e.g., deformation), geometry (e.g., volume), and/or motion of the myocardium during the same time period. The MRI analyzer may play back the series of images associated with the selected MR slice in a section of the second area 204, for example, as an animation (e.g., a cine) along the time axis that the images are taken. Such a two-dimensional plus time (e.g., 2D+T) playback may visualize the movement and/or deformation of the myocardium during the time period associated with the selected MR slice, and the MRI analyzer may provide controls (e.g., in-segment controls such as buttons) on or near the playback area for the user to play, pause, rewind, and/or stop the playback.

In one or more (e.g., all) images of the 2D+T playback, the MRI analyzer may segment the endocardium and/or epicardium and mark the boundaries 206 of the endocardium and/or epicardium along the cardiac cycle. The segmentation and/or marking may be performed using a machine learning (ML) model. Examples of such ML models may be found in commonly assigned U.S. patent application Ser. No. 16/905,115, filed Jun. 18, 2020, entitled "Systems and Methods for Image Segmentation," the disclosure of which is hereby incorporated by reference in its entirety. The MRI analyzer may also allow the user to manually annotate the boundaries of the myocardium. For example, the MRI analyzer may allow the user to plot the entire inner and/or outer boundaries of the myocardium on the one or more images of the selected MR slice or dot certain locations on the inner and/or outer boundaries and trigger the MRI analyzer to automatically connect the dotted locations to form the boundaries. Once the boundaries of the myocardium are determined (e.g., based on either the ML model or manual user inputs), the MRI analyzer may determine or adjust at least a subset of the quantitative parameters described herein such as the strain and/or thickness of the myocardium, based on the determined boundaries. The display of the myocardium boundaries and/or means for manually annotating the myocardium boundaries may be activated and deactivated (e.g., shown or hidden) by the user, for example, using in-segment controls (e.g., a button or checkbox) provided by the MRI analyzer.

The contextual information presented in the second area 204 may include one or more graphs displaying values of the quantitative parameters determined by the MRI analyzer against time. The graphs may be shown, for example, in a section of the second area 204 that is next to the 2D+T animation of the selected MR slice. The graphs may be plotted over the time period associated with the selected MR slice, which, as described herein, may include one or more cardiac cycles. The quantitative parameter values shown in the graphs may include, for example, radial and/or circumferential strains of the myocardium determined by the MRI analyzer based on the selected MR slice (e.g., based on images of myocardium included in the selected MR slice). As such, the graphs may represent radial (Err) and/or circumferential (Ecc) strain curves of the myocardium over the one or more cardiac cycles. The radial strain curve may indicate radially directed myocardial deformation towards the center of a ventricular cavity (e.g., the left ventricular (LV) cavity) over time and the circumferential strain curve may indicate LV myocardial fiber shortening along the circular perimeter observed on the scan axis (e.g., a short-axis) over time. In examples, the circumferential strains may be associated with epicardium, mid-myocardium and/or endocardium, each of which may be displayed as a separate graph (e.g., with a unique color and/or pattern). In examples, the circumferential strains may be determined for a (e.g., any) specific transmural location. For instance, the strain values may be calculated at transmural locations that have shrunk by a certain percentage (e.g., such as 10%) from the epicardium contour along a radial direction. As another example, the strain values may be calculated at transmural locations that have enlarged by a percentage (e.g., such as 10%) from the endocardium contour along a radial direction. Since the strain curves are plotted over a time period that includes one or more diastole phases and one or more systole phases, the curves may provide a visualization of the distribution of myocardial strains during those cardiac phases.

The MRI analyzer may be configured to link (e.g., align) the time frame of a graph to the time frame of the selected MR slice such that one or more points on the graph may be linked to respective images of the selected MR slice, for example, based on alignment of the points and images on the time axis. This way, responsive to a user selecting a point on the graph (e.g., which may indicate an abnormality), the MRI analyzer may automatically adjust (e.g., forward or rewind) the playback of the selected MR slice to show the image that corresponds to the selected point on the graph. The user may thus be able to focus in on the strain value associated with the selected point while also have the image of the myocardium corresponding to the selected point displayed on the side for further investigation.

As described herein, the graphs in the contextual information of the selected MR slice may show characteristics (e.g., strains) of the myocardium over one or more cardiac cycles. The MRI analyzer may be configured to utilize one or more of the following techniques to determine and/or indicate the respective boundaries of the cardiac cycles. The MRI analyzer may allow a user to manually tag frames (e.g., images) that indicate the beginning and/or end of a cardiac cycle. For example, the MRI analyzer may allow the user to mark the end of diastole (ED) and/or end of systole (ES) frames that indicate where a cardiac cycle begins and ends. The MRI analyzer may be configured to learn a model (e.g., a neural network-based model) for automatically detecting the ED and/or ES frames so that the MRI analyzer can indicate the beginning and end of a cardiac cycle in the second area 204 of the display device (e.g., on one or more graphs such as the strain curves displayed in the second area). The MRI analyzer may be configured to determine the ED and/or ES frames based on recorded ECG signals. Tagged ED and ES frames may be indicated using a pre-defined flag. If an automatic detection technique is used (e.g., based on a neural network model or ECG signals) and there is a miscalculation during the automatic detection, the MRI analyzer may allow a user to manually correct the miscalculation (e.g., to manually mark the ED and/or ES frames). Editing a point on a graph (e.g., on the radial or circumferential stain curve shown in FIG. 2) corresponding to a corrected ED frame and/or a corrected ES frame may automatically trigger the MRI analyzer to correct the tracking of strain values in subsequent frames. For example, the strain analysis described herein may be performed from end of diastole to end of systole. As the frame marking the end of diastole or the end of systole in one cardiac cycle is corrected, the MRI analyzer may adjust subsequent strain analysis based on the corrected ED or ES frame. As another example, when myocardium segmentation is performed on a frame-to-frame basis, the MRI analyzer may also adjust the segmentation based on the corrected ED or ES frame. As a result of the auto-correction, errors and/or efforts associated with analyzing the myocardial strains or segmenting the myocardium may be reduced.

The human heart (e.g., the left ventricle) is a 3D structure. While the MR slices described herein may present 2D views of the heart slice by slice along a scan axis, it may also be beneficial to provide a 3D representation of the heart along a time axis (e.g., over the time period associated with the MR slices) based on information captured in the MR slices. The MRI analyzer may determine and display such global information (e.g., 3D plus time or 3D+T information) of the heart in a third area 208 of the display device.

As shown by the example in FIG. 2, the global information may indicate deformation and/or motion of the heart (e.g., the myocardium) across the plurality of MR slices listed in the first area 202 and the MRI analyzer may be configured to the display the global information in manners that demonstrate the deformation and/or motion. For example, in a section of the global information display area (e.g., the third area 208), the MRI analyzer may present a 3D+T view (e.g., a 3D pointcloud plus time, a 3D mesh plus time, a 3D sparse sample point representation plus time, etc.) that may comprise a plurality of representations of a segmented myocardium (e.g., indicated by the dotted lines) over time. Each representation of the segmented myocardium may correspond to a MR slice listed in the first area 202 and the dotted lines in each representation may mark the boundaries of the myocardium as depicted by the MR slice. The MR slice selected in the first area 202 and displayed in the second area 204 may be highlighted in the 3D+T view to indicate the position of the selected MR slice relative to other slices. And since the 3D+T view includes multiple slices of the myocardium, the deformation and/or motion of the myocardium shown by a particular slice (e.g., the selected MR slice) may be inspected in comparison to the other slices included in the view.

The MRI analyzer may render the 3D+T view in various ways to highlight different parts and/or characteristics of the myocardium. For example, the MRI analyzer may display the endocardium and the epicardium in different colors or patterns to distinguish the two parts. When a 2D+T cine is playing in the second area 204 (e.g., for a selected MR slice), the MRI analyzer may adjust the 3D+T view in accordance with the passing of time in the 2D+T cine to display the current state (e.g., the current set of boundary points) of the myocardium corresponding to the frame being played in the 2D+T cine. Such an animated 3D+T representation of the myocardium may supplement the slice view shown in the area 204 (e.g., which corresponds to only a current slice of the myocardium) and allow a user to monitor how the myocardium (e.g., multiple slices of the myocardium) is deforming in real time. The user may be able to pause and/or restart the animated 3D+T display of the myocardium, for example, via a button or another suitable input mechanism provided by the MRI analyzer.

A user of the MRI analyzer may be able to navigate through different slices of the myocardium via the 3D+T view displayed in the areas 208. For example, the user may be able to select a point on the 3D pointcloud or mesh and the MRI analyzer may adjust the display in the first area 202 and/or the second area 204 to display information about the MR slice (e.g., show strain curves) that corresponds to the point selected by the user on the 3D+T view.

The MRI analyzer may be further configured to determine parameters that indicate the global characteristics of the heart (e.g., the myocardium) and display these parameters in a section of the third area 208 to visually indicate the characteristics of the heart. For example, the MRI analyzer may render one or more plots 210 (e.g., bullseye plots) in the third area 208 that demonstrate the strain values associated with different segments of the myocardium (e.g., the left ventricle). In the example shown in FIG. 2, the myocardium is divided into 16 segments (e.g., along horizontal and vertical directions) and projected onto a 2D plane, resulting in the representation shown in plots 210. A minimum, maximum or average strain value may then be calculated for each of the 16 segments over time (e.g., over the time period associated with the MR slices or cine) and displayed in a corresponding area of the plots 210, indicating the cardiac condition (e.g., deformation, motion, etc.) associated with each segment of the myocardium. A value scale may also be provided (e.g., with different color-coding scheme or patterns) and the plots 210 may be color-coded or patterned according to the value scale to indicate where each specific value falls within the value range. Either or both of radial and circumferential strains may be calculated and plotted. Other myocardium function metrics such as strain rates may also be calculated and plotted. The circumferential strains may be measured at different transmural locations including the endocardium, the mid-myocardium, the epicardium, another predefined transmural location described herein, or as the minimum, maximum or average values of all or a subset of these transmural locations.

Figure 3:
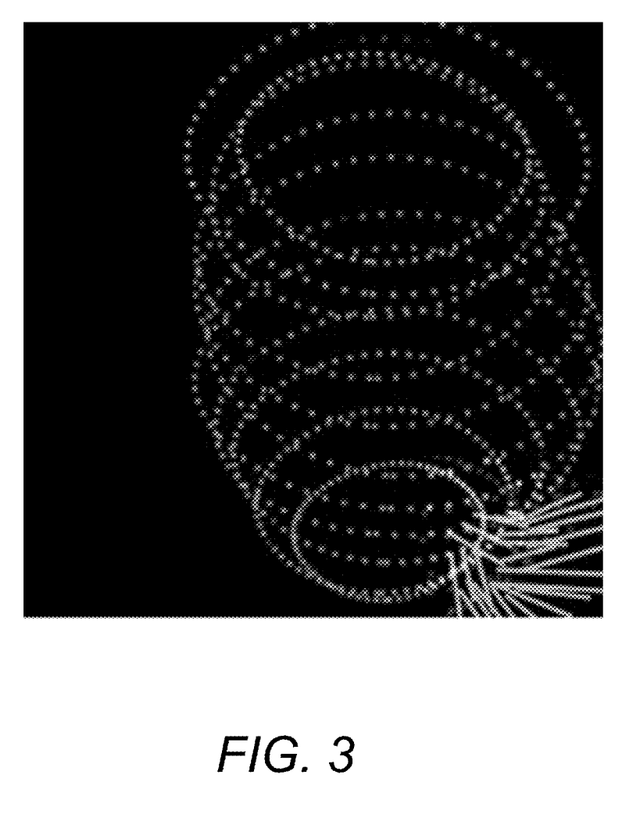
FIG. 3 is a diagram illustrating how a 3D view of a myocardium generated by an MRI analyzer may be highlighted responsive to a user input.

The plots 210 may be rendered such that a user may select a segment on the plots and the corresponding myocardium region in the 3D+T view may be highlighted to give the user an overview of how the region deforms, for example, relative to the other regions of the myocardium. FIG. 3 is simplified diagram illustrating how a section of the myocardium may be highlighted responsive to a user selecting a segment on the plots 210, for example, to indicate the transformation of a key point on the myocardium from an ED phase to an ES phase (e.g., to indicate how much the key point has moved between the phases).

Figure 4:
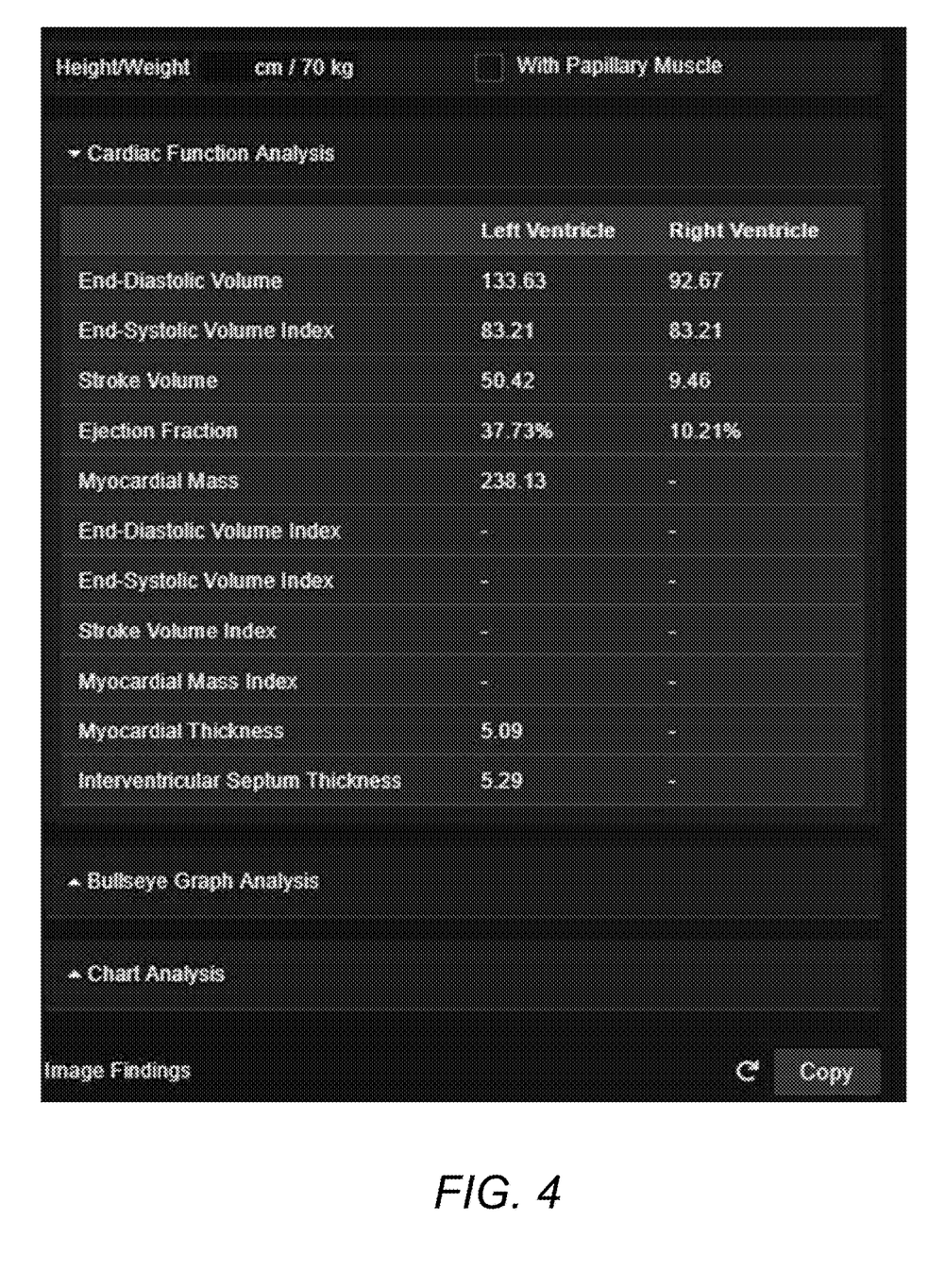
FIG. 4 is diagram illustrating an example user interface that may be rendered by an MRI analyzer described herein.

FIG. 4 shows an example user interface that may be rendered by the MRI analyzer (e.g., the MRI analyzer 106) described herein. The user interface may present basic patient information (e.g., height, weight, etc.) and/or a summary of the cardiac parameters determined by the MRI analyzers. These parameters may be related to cardiac function analysis, bullseye graph analysis, and/or specific chart analysis. For instance, the cardiac function analysis section of the display may show parameter values related to ED volume, ES volume, ejection fraction, myocardial mass, ED volume index, ES volume index, stroke volume index, myocardial volume index, myocardial thickness, interventricular septum thickness, etc.

Figure 5:
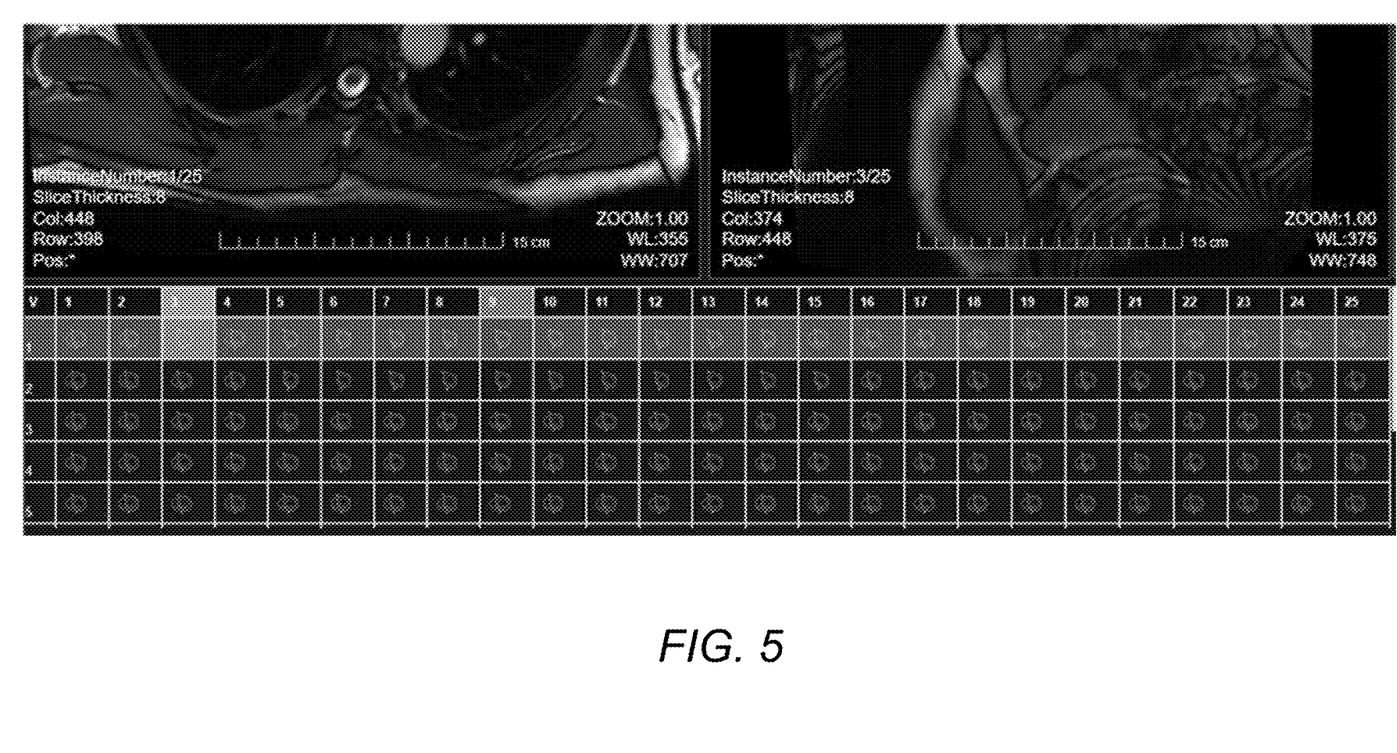
FIG. 5 is a diagram illustrating an example matrix view that may be rendered by an MRI analyzer described herein.

FIG. 5 shows an example matrix view that may be rendered by an MRI analyzer as described herein (e.g., the MRI analyzer 106) based on information determined by the MRI analyzer from an MRI scan of the heart that may show the left ventricle (e.g., the myocardium). The matrix view may be used to present information associated with a plurality of MR slices obtained from the MRI scan. Each row of the matrix may represent a MR slice (e.g., indexed by a row number) and each column of the matrix may represent an image (e.g., indexed by a column number) in an MR slice. Hence, a user of the MRI analyzer may move a cursor across the columns along a row and be presented with an animated display (e.g., a cine movie as shown in area 204 of FIG. 2) of the beating heart in accordance with the MR slice that corresponds to the selected row. Each cell of the matrix may include a visual representation of the state of the myocardium (e.g., analytics associated with the myocardium) at the location and time indicated by the corresponding row (e.g., an MR slice) and column (e.g., an image in the MR slice), respectively. For example, each cell of the matrix may include a respective icon that represents the state of a segment of the human heart (e.g., left ventricle endocardium, epicardium, papillary muscles, right ventricle, etc.) as indicated by the analytics determined by the MRI analyzer. A user may select one or more cells from the matrix and in response, the MRI analyzer may display MRI images (e.g., frames) corresponding to the selected cells (e.g., in a top section of the matrix view) for the user to conduct further analysis.

An MRI analyzer as described herein (e.g., the MRI analyzer 106) may also be configured to generate, transmit and/or print reports of the information determined and/or displayed by the MRI analyzer. Such information may include, for example, an image or an MR slice of the left ventricle or the myocardium, a strain chart, a bullseye plot (e.g., parts of the bullseye plot that correspond to respective segments of the myocardium), a matrix view, and/or underlying data that are used to render the image, slice, chart, plot or view. The report may be generated automatically or semi-automatically. In example implementations, the MRI analyzer may provide a dialog box, e.g., responsive to a user selecting a menu item for report generation, for the user to specify what information is to be included in a report. In example implementations, the MRI analyzer may display an icon as the user hovers a mouse over a data element to indicate that the user may add the data element to a report. For instance, the MRI analyzer may display such an icon responsive to the user hovering a mouse over the bullseye plot 210 shown in FIG. 2 to indicate that the user may add the plot and/or the underlying data used to render the plot to a report. Upon the user clicking on the icon, the MRI analyzer may copy the plot and/or the underlying data to a clipboard. The user may then paste (e.g., using ctrl+v of a computer keyboard) the copied contents to the report that the user is creating. In example implementations, the MRI analyzer may be configured to recognize a user's voice (e.g., oral instructions) regarding report generation and information to be included in the report, translate the voice into text, and display the text in a dialog initiated by the user. The user may then confirm the translation and start the report generation, transmission, and/or printing.

Figure 6:
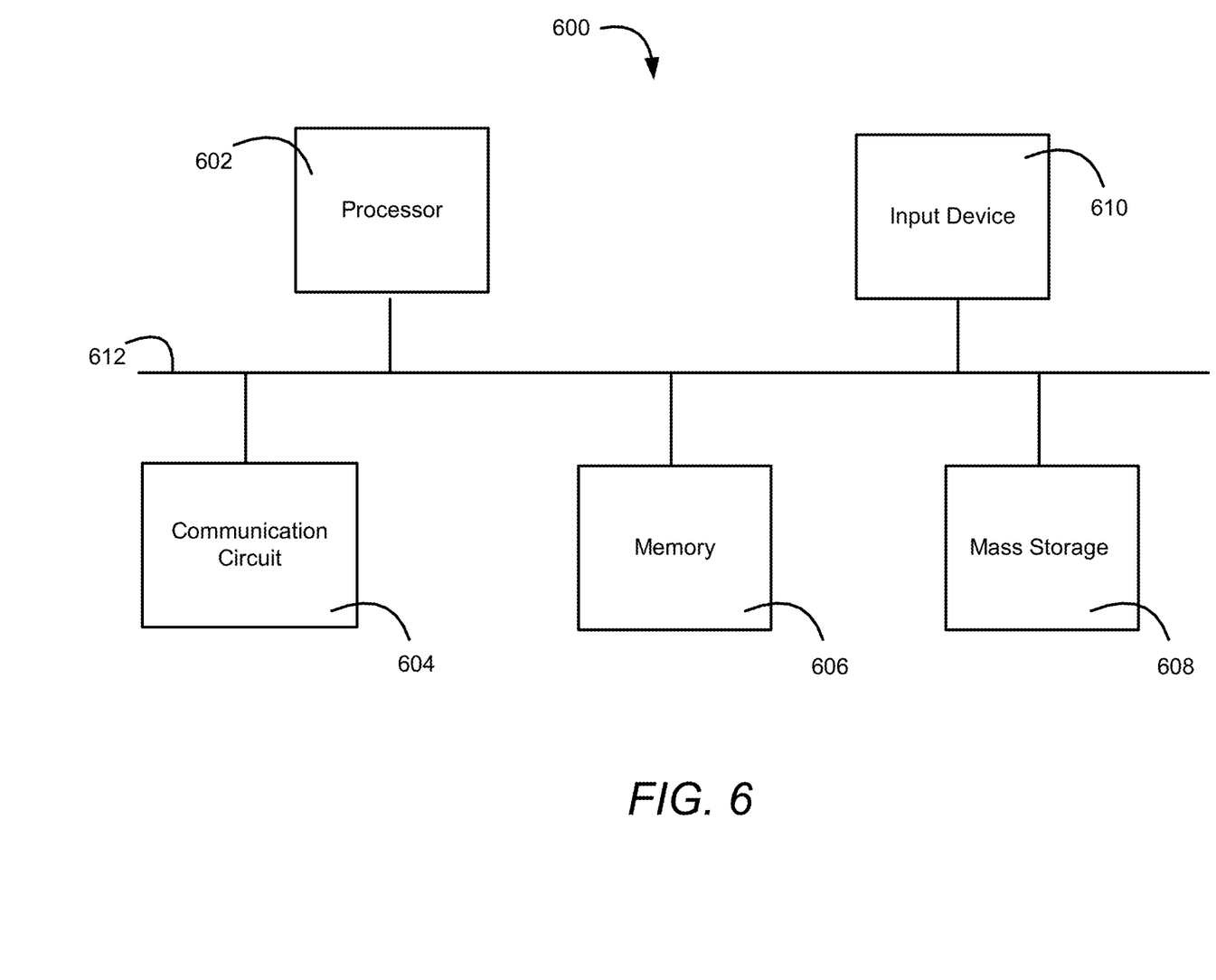
FIG. 6 is a block diagram illustrating an example MRI analyzer described herein.

FIG. 6 is a block diagram illustrating an example MRI analyzer 600 as described herein (e.g., the MRI analyzer 106 in FIG. 1). As shown, the MRI analyzer 600 may include a processor 602, which may be a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. The MRI analyzer 600 may further include a communication circuit 604, a memory 606, a mass storage device 608, an input device 610, and/or a communication link 612 (e.g., a communication bus) over which the one or more components shown in FIG. 6 may exchange information. The communication circuit 604 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 606 may include a storage medium configured to store machine-readable instructions that, when executed, cause the processor 602 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EEPROM)), flash memory, and/or the like. The mass storage device 608 may include one or more magnetic disks such as one or more internal hard disks, one or more removable disks, one or more magneto-optical disks, one or more CD-ROM or DVD-ROM disks, etc., on which instructions and/or data may be stored to facilitate the operation of the processor 602. The input device 610 may include a keyboard, a mouse, a voice-controlled input device, a touch sensitive input device (e.g., a touch screen), and/or the like for receiving user inputs to the neural network system 600.

Figure 7:
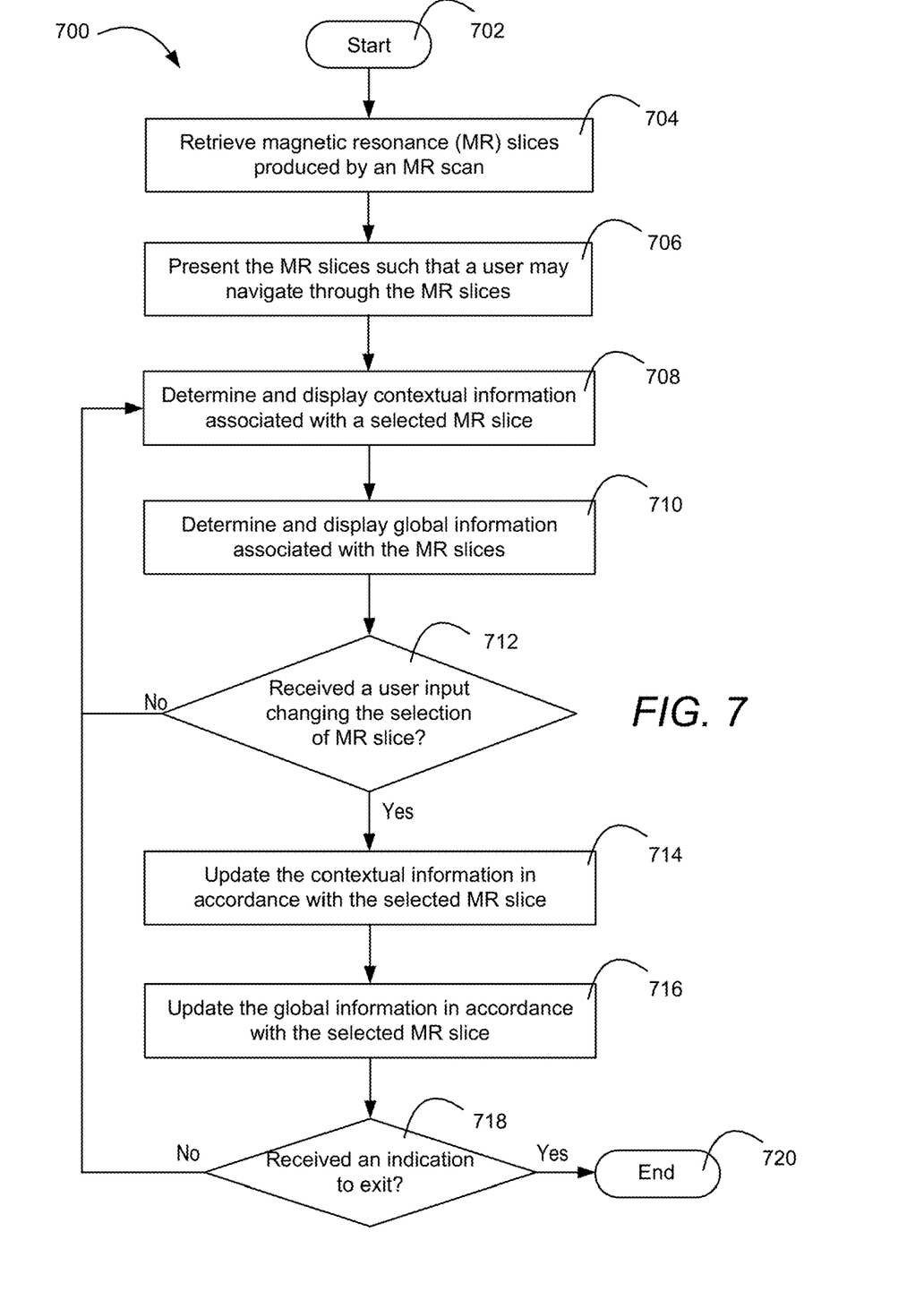
FIG. 7 is a flow diagram illustrating an example process that may be executed by an MRI analyzer described herein.

FIG. 7 is a flow diagram illustrating an example process 700 that may be executed by an MRI analyzer described herein (e.g., the MRI analyzer 106 in FIG. 1 and/or the MRI analyzer 600 in FIG. 6). The process 700 may be started by the MRI analyzer at 702, for example, upon the MRI analyzer being invoked by a user. At 704, the MRI analyzer may retrieve a plurality of MR slices that may be produced by an MRI scan (e.g., a cardiac MR cine). The MR slices may correspond to respective scan locations along a scan axis and each MR slice may include a visual representation of a myocardium over a period of time (e.g., one or more cardiac cycles). At 706, the MRI analyzer may present the MR slices, for example, in a first area of a display device. The presentation may be provided in a way that allows the user of the MRI analyzer to navigate through the MR slices along the scan axis. At 708, the MRI analyzer may determine and display contextual information associated with a selected slice of the plurality of MR slices (e.g., the first MR slice in the series if no user selection is received), for example, in a second area of the display device. The contextual information may include images of the myocardium associated with the selected MR slice and strains of the myocardium indicated by the images. The display of the contextual information may include a playback of the cine movie associated with the selected MR slice and graphs (e.g., strain curves) indicating one or more cardiac parameters determined based on the selected MR slice.

At 710, the MRI analyzer may determine and display global information associated with the myocardium across the plurality of MR slices, for example, in a third area of the display device. The global information may include strain and/or deformation parameters of the myocardium determined by the MRI analyzer based on the plurality of MR slices. The display of the global information may include a 3D view (e.g., a 3D mesh or pointcloud) of the myocardium segmented based on the plurality of MR slices. The display may also include one or more plots (e.g., bullseye plots) that show the global strain or deformation parameters determined by the MRI analyzer for different segments of the myocardium.

At 712, the MRI analyzer may determine whether a user input is received that indicates that the user has selected a different MR slice among the plurality of MR slices. If the determination is that the user has not changed the previously selected slice, the MRI analyzer may continue to display the contextual and global information based on the previously selected MR slice. If the determination is that the user has selected a different MR slice, the MRI analyzer may update the contextual information and the display thereof at 714 in accordance with the newly selected MR slice. The MRI analyzer may also update the global information and the display thereof at 716 based on the newly selected MR slice.

At 718, the MRI analyzer may determine whether a user input is received indicating that the user desires to exit the process 700. If the determination is that no user input is received indicating a desire to exit, the MRI analyzer may continue to display the contextual and global information based on the currently selected MR slice. If the determination is that the user desires to exit the process 700, the MRI analyzer may end the process 700 at 720.

For simplicity of explanation, the operations of the MRI analyzer may have been depicted and described with a specific order. It should be appreciated, however, that these operations may occur in various orders, concurrently, and/or with other operations not presented or described herein. Furthermore, it should be noted that not all operations that the MRI analyzer is capable of performing are depicted and described herein. It should also be noted that not all illustrated operations may be required to be performed by the MRI analyzer.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. A system for analyzing cardiac features, comprising:
one or more processors configured to:
receive a plurality of magnetic resonance (MR) slices derived via a magnetic resonance imaging (MRI) scan, wherein each of the MR slices includes a visual representation of a myocardium over a time period;
present the plurality of MR slices in a first area of a display device, wherein the presentation allows a user of the system to navigate through the plurality of MR slices;
responsive to the user selecting a MR slice among the plurality of MR slices in the first area of the display device, determine contextual information associated with the selected MR slice and global information associated with the myocardium based on the plurality of MR slices, wherein the contextual information includes images of the myocardium associated with the selected MR slice and strains of the myocardium indicated by the images, and wherein the global information indicates deformation of the myocardium across the plurality of MR slices; and
display the contextual information in a second area of the display device and the global information in a third area of the display device, wherein the display of the contextual information in the second area includes an animated presentation of the images of the myocardium associated with the selected MR slice and a strain curve associated with the myocardium, wherein the display of the global information in the third area includes a three-dimensional (3D) view that shows the deformation of the myocardium across the plurality of MR slices, and wherein the one or more processors are further configured to highlight a segment of the myocardium in the 3D view in response to the user selecting an area of the display device that corresponds to the segment of the myocardium or to display contextual information associated with one of the plurality of MR slices in the second area of the display device in response to the user selecting an area of the 3D view that corresponds to the one of the plurality of MR slices.

2. The system of claim 1, wherein the strain curve is rendered along a time axis and the one or more processors are further configured to, responsive to the user selecting a point on the strain curve of the myocardium, adjust the animated presentation of the images of the myocardium to display an image of the myocardium that corresponds to a temporal location of the selected point along the time axis.

3. The system of claim 1, wherein the animated presentation of the images of the myocardium indicates an inner boundary and an outer boundary of the myocardium.

4. The system of claim 3, wherein the one or more processors are further configured to receive user inputs that mark the inner and outer boundaries of the myocardium, the one or more processors further configured to indicate the inner and outer boundaries of the myocardium in the animated presentation based on the user inputs.

5. The system of claim 1, wherein the display of the global information further includes a plot that shows respective strain values associated with multiple segments of the myocardium and wherein the one or more processors are further configured to calculate each of the respective strain values as a maximum, minimum or average strain of a corresponding segment of the myocardium during the time period.

6. The system of claim 1, wherein the strain curve of the myocardium indicates radial or circumferential strains of the myocardium.

7. The system of claim 1, wherein the time period corresponds to a cardiac cycle and the strain curve indicates the strains of the myocardium during the cardiac cycle.

8. The system of claim 7, wherein the one or more processors are further configured to receive user inputs that indicate a starting point or an ending point of the cardiac cycle.

9. The system of claim 1, wherein the one or more processors are further configured to display a matrix comprising a plurality of cells, wherein each of the cells is associated with a row and a column, the row represents a respective MR slice among the plurality of MR slices, the column represents a point in time during the time period associated with respective MR slice, and each of the cells indicate a respective state of the myocardium indicated by the respective MR slice at the point in time.

10. The system of claim 1, wherein the one or more processors are further configured to receive a second plurality of MR slices derived via the MRI scan, indicate on the display device that the second plurality of MR slices is available, and responsive to a user input indicating a selection of the second plurality of MR slices, present the second plurality of MR slices in the first area of the display device.

11. The system of claim 1, wherein the one or more processors are further configured to generate a report that includes at least a portion of the contextual information or a portion of the global information in response to receiving a user input indicating that the portion of the contextual information or the portion of the global information is to be included in the report.

12. A method for analyzing cardiac features, the method comprising:
receiving a plurality of magnetic resonance (MR) slices derived via a magnetic resonance imaging (MRI) scan, wherein each of the MR slices includes a visual representation of a myocardium over a time period;
presenting the plurality of MR slices in a first area of a display device, wherein the presentation allows a user to navigate through the plurality of MR slices;
in response to the user selecting a MR slice among the plurality of MR slices in the first area of the display device, determining contextual information associated with the selected MR slice and global information associated with the myocardium based on the plurality of MR slices, wherein the contextual information includes images of the myocardium associated with the selected MR slice and strains of the myocardium indicated by the images, and wherein the global information indicates deformation of the myocardium across the plurality of MR slices; and
displaying the contextual information in a second area of the display device and the global information in a third area of the display device, wherein the display of the contextual information in the second area includes an animated presentation of the images of the myocardium associated with the selected MR slice and a strain curve of the myocardium, wherein the display of the global information in the third area includes a three-dimensional (3D) view that shows the deformation of the myocardium across the plurality of MR slices, and wherein the method further comprises highlighting a segment of the myocardium in the 3D view in response to the user selecting an area of the display device that corresponds to the segment of the myocardium or displaying contextual information associated with one of the plurality of MR slices in the second area of the display device in response to the user selecting an area of the 3D view that corresponds to the one of the plurality of MR slices.

13. The method of claim 12, wherein the strain curve is rendered along a time axis and the method further comprises, responsive to the user selecting a point on the strain curve, adjusting the animated presentation to display an image of the myocardium that corresponds to a temporal location of the selected point along the time axis.

14. The method of claim 12, wherein the animated presentation of the images of the myocardium indicates an inner boundary and an outer boundary of the myocardium.

15. The method of claim 12, wherein the display of the global information further includes a plot that shows respective strain values associated with multiple segments of the myocardium, and wherein the method further comprises calculating each of the respective strain values as a maximum, minimum or average strain of a corresponding segment of the myocardium during the time period.

16. The method of claim 12, wherein the time period corresponds to a cardiac cycle.

17. The method of claim 12, further comprising displaying a matrix that comprises a plurality of cells, wherein each of the cells is associated with a row and a column, the row represents a respective MR slice among the plurality of MR slices, the column represents a point in time during the time period associated the respective MR slice, and each of the cells indicate a respective state of the myocardium indicated by the respective MR slice at the point in time.

* * * * *